US008133278B2

(12) United States Patent
Atanasoska et al.

(10) Patent No.: US 8,133,278 B2
(45) Date of Patent: Mar. 13, 2012

(54) MEDICAL DEVICES HAVING ELECTRODEPOSITED CONDUCTIVE POLYMER COATINGS

(75) Inventors: Liliana Atanasoska, Edina, MN (US); Chandru Chandrasekaran, Mercer Island, WA (US); Robert W. Warner, Woodbury, MN (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 100 days.

(21) Appl. No.: 12/539,819

(22) Filed: Aug. 12, 2009

(65) Prior Publication Data
US 2010/0042205 A1 Feb. 18, 2010

Related U.S. Application Data (60) Provisional application No. 61/088,799, filed on Aug. 14, 2008.

(51) Int. Cl.
*A61F 2/82* (2006.01)
(52) U.S. Cl. ..................... 623/11.11; 623/1.46
(58) Field of Classification Search .................. None
See application file for complete search history.

(56) References Cited

U.S. PATENT DOCUMENTS

| 5,733,925 A | 3/1998 | Kunz et al. |
| 6,730,699 B2 | 5/2004 | Li et al. |
| 7,899,552 B2 * | 3/2011 | Atanasoska et al. ........ 607/122 |
| 2002/0004060 A1 | 1/2002 | Heublein et al. |
| 2005/0208100 A1 * | 9/2005 | Weber et al. ................ 424/426 |
| 2005/0267560 A1 * | 12/2005 | Bates ............................ 623/1.1 |
| 2006/0013850 A1 | 1/2006 | Domb |
| 2006/0045901 A1 * | 3/2006 | Weber .......................... 424/426 |
| 2007/0060815 A1 * | 3/2007 | Martin et al. ................ 600/372 |
| 2007/0224244 A1 | 9/2007 | Weber et al. |

FOREIGN PATENT DOCUMENTS

| WO | 2005/115496 A1 | 12/2005 |
| WO | 2008/083069 A2 | 7/2008 |

OTHER PUBLICATIONS

Li-Qun Wu, "Chitosan-Mediated and Spatially Selective Electrodeposition of Nanoscale Particles", Langmuir 2005, 21, 3641-3646.
G. Shi et al., "A novel electrically conductive and biodegradable composite made of polypyrrole nanoparticles and polylactide", Biomaterials, Jun. 2004; 25(13): 2477-88.
P. Zarras, "Progress in using conductive polymers as corrosion-inhibiting coatings," Radiation Physics and Chemistry 68 (2003) 387-394.
G. Bereket et al., "Electrochemical synthesis and anti-corrosive properties of polyaniline, poly(2-anisidine), and poly (aniline-co-2-anisidine) films on stainless steel," Progress in Organic Coatings 54 (2005) 63-72.

(Continued)

*Primary Examiner* — Thomas J Sweet
*Assistant Examiner* — Rebecca Straszheim
(74) *Attorney, Agent, or Firm* — Mayer & Williams PC; David B. Bonham; Keum J. Park (57) ABSTRACT

According to one aspect, the present invention provides implantable or insertable medical devices that comprise a substrate and a coating over the substrate that comprises at least one type of conductive polymer and at least one type of additional polymer.

24 Claims, 2 Drawing Sheets

OTHER PUBLICATIONS

N. Anderson, "A new conductive polymer as a replacement for chrome conversion coatings," 2003 Aerospace Coatings Removal and Coatings Conference, May 20-22, 2003, in Colorado Springs, CO, USA.

N. F. Atta, "Electrochemical synthesis, characterization and some properties of a polymer derived from thioflavin S," European Polymer Journal 41 (2005) 3018-3025).

Garner et al., "Polypyrrole—heparin composites as stimulus-responsive substrates for endothelial cell growth", J Biomed. Mater. Res. 44(2) (1999) 121-9.

Garner et al., "Human endothelial cell attachment to and growth on polypyrrole-heparin is vitronectin dependent", Journal of Materials Science: Materials in Medicine 10 (1999) 19-27.

M.A. Lucio Garcia et al., "Study of electrodeposited polypyrrole coatings for the corrosion protection of stainless steel bipolar plates for the PEM fuel cell", Journal of Power Sources 158 (2006) 397-402.

F.F. Bruno et al., "Biomimetic Synthesis of Water Soluble Conductive Polypyrrole and Poly (3,4 ethylenedioxythiophene).", Mat. Res. Soc. Symp. Proc. vol. 736, 2003, D7.13.1-D7.13.6.

X. Pang et al., "Electrodeposition of composite hydroxyapatite—chitosan films", Materials Chemistry and Physics 94 (2005) 245-251.

X. Pang et al., "Fabrication of Composite Films Containing Zirconia and Cationic Polyelectrolytes", Langmuir, 20 (2004) 2921-2927.

J. Wang et al., "Preparation and Characterization of Electrodeposited Calcium Phosphate/Chitosan Coating on Ti6AI4V Plates", J. Dent. Res. 83(4), 2004, 296-301.

Y. Fan et al., "A composite coating by electrolysis-induced collagen self-assembly and calcium phosphate mineralization", Biomaterials 26 (2005) 1623-1632.

C. Boura et al, "Endothelial cell—interactions with polyelectrolyte multilayer films", Biomaterials 26 (2005) 4568-4575.

I. Zhitomirsky, "Electrolytic Deposition of Oxide Films in the Presence of Hydrogen Peroxide", Journal of the European Ceramic Society 19 (1999) 2581-2587.

I. Zhitomirsky et al., "Cathodic Electrodeposition of Ceramic Coatings for Oxidation Protection of Materials at Elevated Temperatures", Canadian Metallurgical Quarterly, 41(4), 2002, 497-506.

N. Nagarajan et al., "Cathodic electrodeposition of MnOx films for electrochemical supercapacitors", Electrochimica Acta 51 (2006) 3039-3045.

I. Zhitomirsky et al. "Electrodeposition of hybrid organic—inorganic films containing iron oxide", Materials Letters, 57 (2003) 1045-1050).

X. Pang et al., "Cathodic electrolytic deposition of zirconia films", Surface & Coatings Technology, 195 (2005) 138-146.

Duncan et al., "Polymer—drug conjugates, PDEPT and PELT: basic principles for design and transfer from the laboratory to clinic", Journal of Controlled Release 74 (2001)135.

Duncan, "The dawning Era of Polymer Therapeutics", Nature Reviews/Drug Discovery, vol. 2, May 2003, 347.

Jaber G. Qasem et al, "Kinetics of Paclitaxel 2'-N-methylpyridinium Mesylate Decomposition", AAPS PharmSciTech 2003, 4(2) Article 21.

T.Y. Zakharian et al., "A Fullerene-Paclitaxel Chemotherapeutic: Synthesis, Characterization, and Study of Biological Activity in Tissue Culture", J. Am. Chem. Soc., 127 (2005) 12508-12509.

Y. Kato et al, "N-succinyl-chitosan as a drug carrier:water-insoluble and water-soluble conjugates", Biomaterials 25(5), 2004, 907-915.

K. Dittmar et al. "Nanostructured Ceramic Coatings for Drug Delivery", European Cells and Materials vol. 13. Suppl. 3, 2007 (p. 37).

M. Bitar et al., "Soluble phosphate glass fibres for repair of bone-ligament interface", Journal of Materials Science: Materials in Medicine 16 (2005) 1131-1136.

A. Rajtar et al., "Hydroxyapatite-coated cardiovascular stents", EuroInterv. 2006, 2, 113-115.

A.G. Dias et al., "In vivo Performance of Biodegradable Calcium Phosphate Glass Ceramics using the Rabbit Model: Histological and SEM Observation", Journal of Biomaterials Applications, vol. 20, 2006, 253-266.

P.W. Serruys et al., "Coronary-Artery Stents", N. Engl. J. Med., 354, 2006, 483-495.

A. Pailleret et al., "Surface Reactivity of Polypyrrole/iron-oxide Nanoparticles: Electrochemical and CS-AFM Investigations", EJ Solid State Electrochem 11 (2007) 1013-1021.

M. Mallouki et al., "Polypyrrole-Fe2O3 nanohybrid materials for electrochemical storage", J Solid State Electrochem 11 (2007) 398-406.

B.L. Frankamp, "Surface Modification Using Cubic Silsesquioxane Ligands. Facile Synthesis of Water-Soluble Metal Oxide Nanoparticles", Chem. Mater. 18 (2006) 956-959.

Z. Wang et al., "A biodegradable electrical bioconductor made of polypyrrole nanoparticle/poly(D,L-lactide) composite: A preliminary in vitro biostability study", Journal of Biomedical Materials Research Part A, vol. 66A, Issue 4, 2003, 738-746.

D.D. Allison et al., "Review. Hyaluronan: A Powerful Tissue Engineering Tool", Tissue Engineering, 12(8), 2006, 2131-2140.

B.S. Ong et al., "Structurally Ordered Polythiophene Nanoparticles for High-Performance Organic Thin-Film Transistors," Advanced Materials, 17(9), 2005, 1141-1144.

S.Y. Park et al., "Synthesis and electrical characteristics of polyaniline nanoparticles and their polymeric composite," Current Applied Physics, 4(6), 2004, 581-583.

S. E. Moulton et al., "Polymerisation and characterisation of conducting polyaniline nanoparticle dispersions," Current Applied Physics, 4(2-4), 2004, 402-406.

H,. Xia et al., "Synthesis and Characterization of Conductive Polyaniline Nanoparticles Through Ultrasonic Assisted Inverse Microemulsion Polymerization," Journal of Nanoparticle Research, 3(5-6 ), 2001, 399-409.

J.W. Choi et al., "Poly(3,4-ethylenedioxythiophene) nanoparticles prepared in aqueous DBSA solutions," Synthetic Metals, 141(3), 2004, 293-299.

Y. Yang et al., "Conducting polymeric nanoparticles synthesized in reverse micelles and their gas sensitivity based on quartz crystal microbalance," Polymer, vol. 48, Issue 15, 2007, 4459-4465.

J. Cao et al., "Electrodeposition of composite iron oxide—poly (allylamine hydrochloride) films", Materials Chemistry and Physics 96 (2006) 289-295.

S.P. Armes et al., "Dispersions of electrically conducting polypyrolle particles in aqueous media", J. Chem. Soc., Chem. Commun., 1987, 288-290.

M.L. Digar et al., "Conducting polypyrrole particles dispersible in both aqueous and non-aqueous media" J. Chem. Soc., Chem. Commun., 1992, 18-20.

A.S. Zahr et al., "Encapsulation of Paclitaxel in Macromolecular Nanoshells", Biomacromolecules, 8(6), 2007, 2004-2010.

* cited by examiner

MEDICAL DEVICES HAVING ELECTRODEPOSITED CONDUCTIVE POLYMER COATINGS

RELATED APPLICATIONS

This application claims priority from U.S. provisional application 61/088,799, filed Aug. 14, 2008, which is incorporated by reference herein in its entirety.

FIELD OF THE INVENTION

The present invention relates to medical devices and more particularly to implantable or insertable medical devices having electrodeposited coatings.

BACKGROUND OF THE INVENTION

Implantable and insertable medical devices are commonly provided with one or more coatings which may serve a wide variety of functions including, for example, imparting biocompatibility, enabling drug delivery, providing lubricity, and so forth.

Figure 1A:
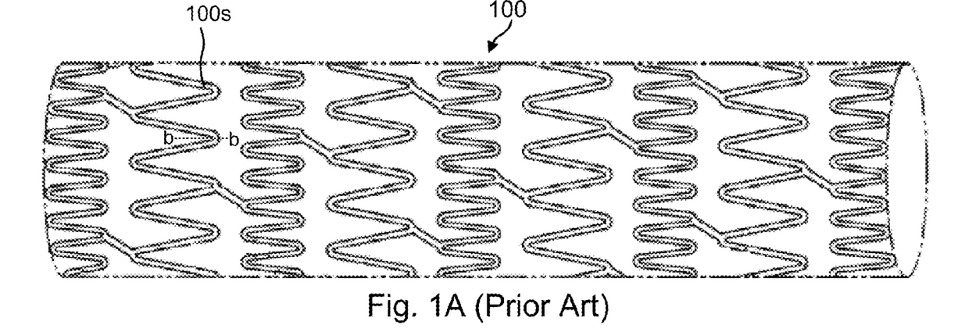
FIG. 1A is a schematic perspective view of a stent in accordance with the prior art.
Figure 1B:
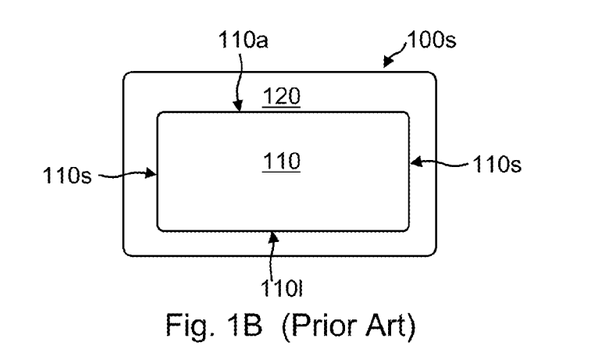
FIG. 1B is a schematic cross-sectional view taken along line b-b of FIG. 1A.

As one specific example (among many others), coronary stents such as those commercially available from Boston Scientific Corp. (TAXUS and PROMUS), Johnson & Johnson (CYPHER), and others are frequently prescribed for maintaining blood vessel patency. These products are based on metallic expandable stents with polymer coatings, which release antiproliferative therapeutic agents at a controlled rate and total dose for preventing restenosis of the blood vessel. One such device is schematically illustrated, for example, in FIGS. 1A and 1B. FIG. 1A is a schematic perspective view of a stent 100 which contains a number of interconnected struts 100s. FIG. 1B is a cross-section taken along line b-b of strut 100s of stent 100 of FIG. 1A, and shows a stainless steel strut substrate 110 and a therapeutic-agent-containing polymeric coating 120, which encapsulates the entire stent strut substrate 110, covering the luminal surface 110l (i.e., the inner, blood-contacting surface), the abluminal surface 110a (i.e., the outer, vessel-wall-contacting surface), and side 110s surfaces thereof.

One recent development in metallic implants is to base such implants on metallic alloys that degrade in vivo. For example as described in U.S. Patent App. Pub. No. 2002/0004060 A1, entitled "Metallic implant which is degradable in vivo," implants may be formed from pure metals or metal alloys whose main constituent is selected from alkali metals, alkaline earth metals, iron, and zinc. Particularly preferred are metals and metal alloys containing magnesium, iron or zinc as a main constituent and one or more additional constituents selected from the following: alkali metals such as Li, alkaline-earth metals such as Ca and Mg, transition metals such as Mn, Co, Ni, Cr, Cu, Cd, Zr, Ag, Au, Pd, Pt, Re, Fe and Zn, Lanthanides such as La and Ce, Group IIIa metals such as Al, and Group IVa elements such as C, Si, Sn and Pb. Of these, magnesium alloys have high corrosion (biodegradation) rates, particularly in the presence of NaCl, which is found in vivo.

SUMMARY OF THE INVENTION

According to one aspect, the present invention provides implantable or insertable medical devices that comprise a substrate and a coating over the substrate that comprises at least one type of conductive polymer and at least one type of additional polymer.

In some embodiments, the present invention provides implantable or insertable medical devices that comprise a biodegradable metallic substrate and a coating over the substrate that comprises at least one type of conductive polymer species (e.g., conductive polymer particles, conductive block copolymers, conductive polymer complexes, etc.) within a polymeric matrix that comprises at least one type of additional polymer.

In some embodiments, the present invention provides implantable or insertable medical devices that comprise a conductive substrate and an electrodeposited coating over the substrate that comprises at least one type of conductive polymer and at least one type of cationic polyelectrolyte.

In those embodiments where the substrate contains a biodegradable metal, the conductive-polymer-containing coatings of the invention can act to control the corrosion rate of the biodegradable metal.

In those embodiments where the conductive-polymer-containing coatings further comprise one or more therapeutic agents, the coatings can act as reservoirs for the therapeutic agents.

Other aspects of the invention concern methods of making and using such devices.

The above and other aspects, embodiments and advantages of the present invention will become immediately apparent to those of ordinary skill in the art upon review of the Detailed Description and any claims to follow.

DETAILED DESCRIPTION OF THE INVENTION

According to one aspect, the present invention provides implantable or insertable medical devices that comprise a substrate and a conductive-polymer-containing coating over the substrate that comprises at least one type of conductive polymer and at least one type of additional polymer. In certain embodiments, the conductive-polymer-containing coating optionally further includes one or more types of inorganic material and optionally further includes one or more types of therapeutic agent. As seen below, for purposes of the present disclosure, the conductive polymer, the additional polymer, the optional inorganic material and the optional therapeutic agent may be, independently, covalently bound to one another, or they may be associated with one another via non-covalent interactions.

In various embodiments, the present invention provides implantable or insertable medical devices that comprise a biodegradable metallic substrate and a conductive-polymer-containing coating over the substrate that comprises at least one type of conductive polymer species (e.g., conductive polymer particles, conductive block copolymers, conductive polymer complexes, etc.) within a polymeric matrix that comprises at least one type of additional polymer.

In various embodiments, the present invention provides implantable or insertable medical devices that comprise a conductive substrate and an electrodeposited conductive-polymer-containing coating over the substrate that comprises at least one type of conductive polymer and at least one type of cationic polyelectrolyte.

The conductive-polymer-containing coatings of the invention may vary widely in thickness, for example, ranging from 100 nm or less to 250 nm to 500 nm to 1 micron to 2.5 microns to 5 microns to 10 microns or more. The coatings may be single-layer or multi-layer coatings.

As used herein "electrodeposition" is the deposition of a material that occurs upon the application of an electrical potential between two conductive materials (or electrodes) within a liquid medium containing charged species. In various embodiments of the invention, materials are electrodeposited at the cathode (i.e., the electrode where reduction takes place). A typical apparatus for carrying out electrodeposition includes the following: an anode, a cathode and, frequently, a reference electrode, each separated by an electrolyte (e.g., an ion containing solution), as well as a potentiostat which monitors/sets the voltages/currents at the various electrodes. Electrodeposition can be carried out under a variety of electrochemical conditions including the following, among others: (a) constant current, (b) constant voltage, (c) current scan/sweep, e.g., via a single or multiple scans/sweeps, (d) voltage scan/sweep, e.g., via a single or multiple scans/sweeps, (e) current square waves or other current pulse wave forms, (f) voltage square waves or other voltage pulse wave forms, and (g) a combination of different current and voltage parameters.

Examples of medical devices benefiting from the conductive-polymer-containing coatings of the present invention vary widely and include implantable or insertable medical devices, for example, stents (including coronary vascular stents, peripheral vascular stents, cerebral, urethral, ureteral, biliary, tracheal, gastrointestinal and esophageal stents), catheters (e.g., urological catheters or vascular catheters such as balloon catheters and various central venous catheters), guide wires, balloons, filters (e.g., vena cava filters and mesh filters for distil protection devices), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), septal defect closure devices, myocardial plugs, patches, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", orthopedic prosthesis such as bone grafts, bone plates, fins and fusion devices, orthopedic fixation devices such as interference screws in the ankle, knee, and hand areas, tacks for ligament attachment and meniscal repair, rods and pins for fracture fixation, screws and plates for craniomaxillofacial repair, artificial ligaments, joint prostheses, dental implants, or other devices that are implanted or inserted into the body.

As indicated above, the present invention provides implantable or insertable medical devices that comprise a substrate and a conductive-polymer-containing coating over the substrate that comprises at least one type of conductive polymer and at least one type of additional polymer.

In many embodiments, the substrates are at least partially conductive. In such embodiments, the substrate, for example, may consist entirely of conductive material, may include a combination of conductive and non-conductive materials (e.g., a conductive coating on a non-conductive material), and so forth. Thus, where a medical device substrate is non-conductive, one may deposit a conductive layer on the device substrate (e.g., a gold sputtered layer, etc.) for purposes of electrodeposition.

Conductive materials include conductive polymeric materials and conductive metallic materials, among others. Examples of conductive polymeric materials are described further below.

Examples of conductive metallic materials include the following: (a) substantially pure metals, including gold, platinum, palladium, iridium, osmium, rhodium, titanium, zirconium, tantalum, tungsten, niobium, ruthenium, alkaline earth metals (e.g., magnesium), iron and zinc, and (b) metal alloys, including metal alloys comprising iron and chromium (e.g., stainless steels, including platinum-enriched radiopaque stainless steel), niobium alloys, titanium alloys, nickel alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys), and biodegradable metal alloys such as metal alloys whose main constituent is selected from alkali metals, alkaline earth metals, iron, and zinc, for example, metal alloys containing magnesium, iron or zinc as a main constituent and one or more additional constituents selected from the following: alkali metals such as Li, alkaline-earth metals such as Ca and Mg, transition metals such as Mn, Co, Ni, Cr, Cu, Cd, Zr, Ag, Au, Pd, Pt, Re, Fe and Zn, Lanthanides such as La and Ce, Group 13 metals such as Al, and Group 14 elements such as C, Si, Sn and Pb.

As noted above, in embodiments where the substrate comprises a biodegradable metallic material, the conductive-polymer-containing coatings of the invention can act to control the corrosion rate of the same.

For example, it is known from several studies that coatings containing conductive polymers (e.g., polypyrrole, among others), are able to provide corrosion protection for metals. Moreover, even coatings with a low percentage of the conductive polymer have been shown to provide significant corrosion protection, although the degree of protection offered by conductive coatings has been observed to be influenced by the amount of conductive polymer within such composites. For example, G. Shi et al., *Biomaterials,* 2004 June; 25(13): 2477-88, have reported an electrically conductive biodegradable composite material made of poly(d,l-lactide) and polypyrrole nanoparticles, which has a surface resistivity as low as $1\times10^3$ Ω/square. The material was prepared by emulsion polymerization of pyrrole in a poly(d,l-lactide) solution (in $CHCl_3$), followed by precipitation and casting onto a substrate. A conductivity increase of six orders of magnitude was observed to accompany an increase in polypyrrole content from 1% to 17%.

By way of background, many of the conductive polymers used in corrosion protection fall within the following classes: polyaniline and its derivatives and copolymers, poly(phenylene vinylene) and its derivatives and copolymers, and polyheterocycles and their derivatives and copolymers. Conductive polymers are commonly transformed from an insulating state to a conducting state through doping. Techniques for doping include, for example, (1) chemical doping by charge transfer, (2) electrochemical doping, (3) doping by acid-base chemistry (e.g., polyaniline undergoes this form of doping), and (4) photodoping, among others.

For example, polyaniline (PANI) is normally prepared as the conductive emeraldine salt (ES) from both chemical and electroelectrochemical polymerization techniques. By treatment with base the emeraldine base (EB) form can be obtained. The doping process used to increase and decrease the electrical conductivity of PANI is typically by protonation (doping) and de-protonation (de-doping). Both the doped and undoped forms of PANI have been shown to provide corrosion protection. For further information, see, e.g., P. Zarras, "Progress in using conductive polymers as corrosion-inhibiting coatings," *Radiation Physics and Chemistry* 68 (2003) 387-394 and the references cited therein. Examples of PANI copolymers include poly(aniline-co-2-anisidine) reported in G. Bereket et al., "Electrochemical synthesis and anti-corrosive properties of polyaniline, poly(2-anisidine), and poly (aniline-co-2-anisidine) films on stainless steel," *Progress in Organic Coatings* 54 (2005) 63-72, among others.

Among poly(phenylene vinylenes) (PPV), backbone-modified poly(bis-dialkylamino)phenylene vinylene) (BAM-PPV) has been used to form corrosion resistant conductive polymeric coatings. BAM-PPV is reported to be effective in neutral to basic conditions. For further information, see, e.g., N. Anderson, "A new conductive polymer as a replacement for chrome conversion coatings," 2003 *Aerospace Coatings Removal and Coatings Conference*, May 20-22, 2003, in Colorado Springs, Colo., USA.

Polyheterocycles for use in conductive polymeric coatings include polypyrrole (PPy), polythiophene and their derivatives and copolymers. As with PANI and PPV above, it is known to modify the polymer backbone of these materials through the introduction of various functional groups (for instance, poly(3-alkyl pyrrole) and poly(3-alkyl thiophene) are examples of alkyl derivatives), and chemical or electrochemical polymerization techniques may be employed to form such polymers. For further information, see, e.g., P. Zarras, supra, and references cited therein. Another example of a polythiophene derivative is poly(3,4-ethylenedioxythiophene) (PEDOT).

Additional examples of conductive polymers include poly (2-anisidine) (see, e.g., G. Bereket et al., supra) and poly (thioflavin S) (see, e.g., N. F. Atta, "Electrochemical synthesis, characterization and some properties of a polymer derived from thioflavin S," *European Polymer Journal* 41 (2005) 3018-3025), among others.

Using the above and other conductive polymers, corrosion resistant coatings may be provided on conductive substrates in accordance with the invention.

Coatings in accordance with the invention may comprise, for example, from 5 wt % or less to 10 wt % to 25 wt % to 50 wt % to 75 wt % or more of one or more types of conductive polymer.

In addition to reducing corrosion in metallic materials, conductive polymers have also been reported to encourage cell growth. In particular, polypyrrole has been observed to support the proliferation of endothelial cells. See, e.g., Garner et al., *J Biomed. Mater. Res.* 44(2) (1999) 121-9 and Garner et al., *Journal of Materials Science: Materials in Medicine* 10 (1999) 19-27.

In certain embodiments of the invention, conductive-polymer-containing coatings are formed on substrates that comprise (or consist entirely of) biodegradable metallic materials. For example, a biodegradable metallic stent may be provided with a conductive-polymer-containing coating in accordance with the invention. This may provide the ability to fine-tune the corrosion rate (and thus the biodegradation rate) of the stent, among other features. In addition to delaying corrosion, such coatings may also promote substantial endothelial cell growth at the site of the implant.

Anodic electrodeposition is a common process for forming coatings of conductive polymers such as polypyrrole on metallic surfaces. However, the anodic electrodeposition of conductive polymers on biodegradable metals (e.g., magnesium, iron, zinc, their alloys, etc.) is complicated by the fact that the metals tends to undergo anodic dissolution before the electropolymerization potential of the monomer (e.g., pyrrole) is reached. In other words, the oxidation potential of the metal is significantly more negative than that of pyrrole. Therefore, metal dissolution occurs and stabilizes the potential of the electrode at values that prevent monomer oxidation. Usually this is resolved by forming a partial passivation of the metal to decrease its dissolution rate. For many metallic materials, however, it is not possible to grow polypyrrole directly at anodic currents and potentials, because severe anodic dissolution of the metallic material occurs, which cannot be prevented using passivation measures.

In accordance with one aspect of the present invention, this problem may be overcome by depositing conductive-polymer-containing coatings at cathodic, rather than anodic, potentials. Materials (e.g., one or more types of type of conductive polymer, one or more types of additional polymer, one or more types of optional inorganic material, one or more types of optional therapeutic agent, etc.) may be cathodically electrodeposited on conductive substrates by a variety of mechanisms including, for example, the following, among other mechanisms: (a) electrophoresis (e.g., migration of a positively charged species to the cathode), (b) cathodic reduction of a soluble species such that it forms an insoluble species, (c) cathodic reactions resulting in pH gradients that cause soluble species to become insoluble and (d) entrapment (e.g., as a result of electrodeposition of another material at the cathode).

In accordance with various embodiments of the present invention, a variety of conductive polymer materials (e.g., selected from those described above, among others) are cathodically electrodeposited on conductive substrates.

In certain embodiments, conductive polymers are provided in particulate form for cathodic deposition. Conductive polymer particles for use in the invention may vary widely in size. Commonly, they are nanoparticles, meaning that they have at least one major dimension (e.g., the thickness for nanoplates, the diameter for nanospheres and nanotubes, etc.) that is less than 1000 nm, and in certain embodiments, less than 100 nm. For example, nanoplates typically have at least one dimension (e.g., thickness) that is less than 1000 nm, other nanoparticles typically have at least two orthogonal dimensions (e.g., thickness and width for nanoribbons, diameter for nanocylinders and nanotubes, etc.) that are less than 1000 nm, while still other nanoparticles typically have three orthogonal dimensions that are less than 1000 nm (e.g., the diameter for nanospheres).

Several known techniques for forming conductive polymer particles are described here, among many other possibilities.

For example, polypyrrole nanoparticles may be formed using an oxidant such as $FeCl_3$. Polymers that may be used as stabilizers for polypyrrole particle dispersions include polyvinyl alcohol, poly(vinyl alcohol-co-vinyl acetate), poly(vinylpyrrolidone), poly(acrylamide), poly(ethylene oxide), poly(ethylene glycol)/poly(tetramethylene ether glycol) multiblock copolymer, poly(vinyl methyl ether), and methylcellulose. See, e.g., S. P. Arms et al., *J. Chem. Soc., Chem. Commun.,* 1987, 288-290, wherein conducting polypyrrole particles of 50-250 nm diameter are prepared by dispersion polymerization in aqueous media using $FeCl_3$ as initiator-dopant. See also, e.g., M. L. Digar et al., "Conducting polypyrrole particles dispersible in both aqueous and non-aqueous media" *J. Chem. Soc., Chem. Commun.,* 1992, 18-20.

Methods are also known for forming nanoparticles from various other conductive polymers besides polypyrrole, including the following, among others: (a) thiophene (see, e.g., B. S. Ong et al., "Structurally Ordered Polythiophene Nanoparticles for High-Performance Organic Thin-Film Transistors," *Advanced Materials,* 17(9), 2005, 1141-1144); (b) polyaniline (see, e.g., S. Y. Park et al., "Synthesis and electrical characteristics of polyaniline nanoparticles and their polymeric composite," *Current Applied Physics,* 4(6), 2004, 581-583, S. E. Moulton et al., "Polymerisation and characterisation of conducting polyaniline nanoparticle dispersions," *Current Applied Physics,* 4(2-4), 2004, 402-406, and H., Xia et al., "Synthesis and Characterization of Conductive Polyaniline Nanoparticles Through Ultrasonic Assisted Inverse Microemulsion Polymerization," *Journal of Nanoparticle Research,* 3(5-6), 2001, 399-409); and (c) PEDOT (see, e.g., J. W. Choi et al., "Poly(3,4-ethylenedioxythiophene) nanoparticles prepared in aqueous DBSA solutions," *Synthetic Metals,* 141(3), 2004, 293-299 and Y. Yang et al., "Conducting polymeric nanoparticles synthesized in reverse micelles and their gas sensitivity based on quartz crystal microbalance," *Polymer,* Volume 48, Issue 15, 2007, 4459-4465).

In certain embodiments, conductive polymer particles may be electrodeposited via a mechanism that includes electromigration toward the cathode due to the electric field that exists in the solution. In these embodiments, the particles positively charged.

Examples of charged particles include those that are charged as formed. For instance, conductive particles may be formed using a cationic surfactant as a dispersing agent during the particle formation process.

Further examples of charged particles include those that are modified to have a charge using any suitable technique. For instance, particles may be made positively charged by applying a layer of a positively charged material to previously formed particles. For example, a variety of particles may be positively charged by exposure to (and adsorption of) a cationic polyelectrolyte such as poly(allyamine hydrochloride) (PAH), polyethyleneimine (PEI), poly(diallyldimethylammonium chloride) (PDDA) or chitosan, among others. If desired, the charge on a particle can be reversed by exposing it to a solution containing a polyelectrolyte of opposite charge.

As a further example, cationic polyelectrolytes may be covalently attached to particles (e.g., via "grafting to" or "grafting from" techniques). In these embodiments, the cationic polyelectrolyte is covalently bound to the conductive polymer.

In certain other embodiments, conductive polymers may be provided in soluble form for cathodic deposition. For example, deposition may be conducted based on water soluble complexes of polypyrrole or poly(3,4-ethylenedioxythiophene) formed in a procedure analogous to that described in F. F. Bruno et al., *Mat. Res. Soc. Symp. Proc.* Vol. 736, 2003, D7.13.1-D7.13.6 using poly(ethylene glycol) modified hematin (PEG-Hematin) as a catalyst and a suitable polyelectrolyte (which provides water solubility). However, rather than conducting the polymerization in the presence of an anionic polyelectrolyte such as polystyrene sulfonate, a cationic polyelectrolyte such as chitosan, PAH, PEI or PDDA, among others, may be employed to render the product amenable to cathodic deposition.

In certain other embodiments, conductive block copolymers may be formed in which at least one conductive polymer (i.e., at least one conductive polymer block) is covalently attached to at least one cationic polyelectrolyte (i.e., at least one cationic polyelectrolyte block).

For example, copolymers have been formed from hyaluran (a polysaccharide) and polypyrrole. See D. D. Allision et al., and *Tissue Engineering,* 12(8), 2006, 2131-2140 and the references cited therein. Substitution of a cationic polyelectrolyte such as chitosan would create a copolymer of a cationic polyelectrolyte and a conductive polymer.

As will be appreciated from the discussion to follow, in cases where a conductive polymer is formed into a soluble species (e.g., a soluble complex, soluble block copolymer, soluble particle dispersion, etc.) via association with a cationic polyelectrolyte (e.g., by covalent binding, adsorption, complex formation, etc.), depending on the associated cationic polyelectrolyte, the polyelectrolyte may loose its charge due to an increase in pH as it migrates to the cathode, causing the soluble species to become insoluble. This mechanism may be used achieve/enhance conductive polymer deposition at the cathode.

In other embodiments, neutral conductive-polymer-containing species (e.g., neutral complexes, neutral soluble copolymers, neutral particle suspensions, etc.) that are present in solution at the cathode may be captured and incorporated (i.e., entrapped) during electrodeposition. For example such conductive-polymer-containing species may be entrapped during electrodeposition of a cationic polyelectrolyte material (e.g., during the deposition of chitosan, collagen, PAH, or another cationic polyelectrolyte as discussed below), among many other possibilities.

As previously noted, in addition to one or more types of conductive polymer, electrodeposited coatings in accordance with the invention further include one or more types of additional polymer. The coatings may comprise, for example, from 25 wt % or less to 50 wt % to 75 wt % to 90 wt % to 95 wt % or more of such additional polymers.

In many embodiments, the additional polymer is a cationic polyelectrolyte. As used herein, "polyelectrolytes" are polymers having multiple (e.g., 5 to 10 to 25 to 50 to 100 to 250 to 500 to 1000 or more) charged groups (e.g., ionically dissociable groups that provide cations and anions), at least over a certain pH range. Frequently, the number of charged groups is so large that the polymers are soluble in aqueous solutions when in ionically dissociated form (also called, for example, polyions, polycations or polyanions). Polyelectrolytes include polyacids and polybases (and their salts). When dissociated, polyacids form polyanions (anionic polyelectrolytes), with protons being split off. Polybases contain groups which are capable of accepting protons, forming polycations (cationic polyelectrolytes).

Some polyelectrolytes have both anionic and cationic groups, but nonetheless have a net negative charge at certain pH values, for example, because the anionic groups outnumber the cationic groups, or have a net positive charge, for example, because the cationic groups outnumber the anionic groups. In this regard, the net charge of a particular polyelectrolyte may change in sign with the pH of its surrounding environment, for example, changing (with increasing pH) from a positive net charge, to a neutral net charge (known as the isoelectric point) to a net negative charge. Various proteins and proteins are polyelectrolytes of this type, existing as cationic polyelectrolytes at pH values below than their isoelectric points.

Thus, as defined herein, the term "polyelectrolyte" embraces a wide range of species, including polycations and their precursors (e.g., polybases, polysalts, etc.), polyanions and their precursors (e.g., polyacids, polysalts, etc.), polymers having both anionic and cationic groups (e.g., polymers having multiple acidic and basic groups such as are found in various proteins and peptides), ionomers (polyelectrolytes in which a small but significant proportion of the constitutional units carry charges), and so forth.

Cationic polyelectrolytes include those that have a net positive charge at least at pH values$\leq 4$. Cationic polyelectrolytes thus include those that are positively charged over any of the following pH ranges: pH$\leq 4$, pH$\leq 5$, pH$\leq 6$, pH$\leq 7$, pH$\leq 8$, pH$\leq 9$, pH$\leq 10$, pH$\leq 11$, pH$\leq 12$, and so forth. Stronger cationic polyelectrolytes (also called strong polybases) can maintain a positive charge at greater pH values than weaker cationic polyelectrolytes. Typically, for strong cationic polyelectrolytes, the positive charge is practically independent of pH. The positive charge of weak cationic polyelectrolytes, on the other hand, is strongly dependent on the pH of the surrounding environment. For example, chitosan, discussed below, is a weak cationic polyelectrolyte. It is positively charged and water-soluble in acidic to near-neutral solutions, but it becomes substantially uncharged (and loses its water-solubility) at pH values of about 6.5 and above. Similarly, collagen, with an isoelectric point of pH 5.5, is positively charged (i.e., it is a cationic polyelectrolyte) at slightly acidic pH, but it is substantially insoluble in water at neutral pH. Other examples of weak cationic polyelectrolytes include PAH and PEI, among many others. An example of a strong cationic polyelectrolyte is PDDA, among many others.

Specific examples of suitable polycations may be selected, for instance, from the following: polyamines, including polyamidoamines, poly(amino methacrylates) including poly(dialkylaminoalkyl methacrylates) such as poly(dimethylaminoethyl methacrylate) (PDMAEMA) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine hydrochloride) (PAH), poly(diallyldialklylamines) such as poly(diallyldimethylammonium chloride) (PDDA), polyvinyl ether of monoethanolamine (PVEMEA), spermine, spermidine, hexadimethrene bromide (polybrene), polyimines including polyalkyleneimines such as polyethyleneimine (PEI), polypropyleneimines and ethoxylated polyethyleneimines, polycationic peptides and proteins, including histone polypeptides and homopolymer and copolymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, and poly-L,D-ornithine, gelatin, collagen, albumin, protamine and protamine sulfate, and polycationic polysaccharides such as cationic starch and chitosan, as well as copolymers, derivatives and combinations of the preceding, among various others. Certain of the above polyelectrolytes, including various bio-polyelectrolytes, are biodegradable.

As previously noted, in addition to one or more types of conductive polymer and one or more types of additional polymer, electrodeposited coatings in accordance with the invention may optionally further include one or more types of inorganic materials. The coatings may comprise, for example, from 5 wt % or less to 10 wt % to 25 wt % to 50 wt % or more of such optional inorganic materials.

The inclusion of inorganic materials may be advantageous in that hybrid materials may be formed which have increased biocompatibility, increased bioactivity and/or increased robustness vis-à-vis counterpart materials which do not contain inorganic materials. With respect to robustness, the inorganic materials can, for example, provide wear resistance, whereas the polymeric materials can address brittleness that may otherwise be associated with the inorganic materials.

Examples of inorganic materials include biostable and biodegradable inorganic materials such as metal phosphates (e.g., calcium phosphate species such as hydroxyapatite, calcium phosphate glass ceramics, magnesium phosphate, iron phosphate, zinc phosphate, zirconium phosphate, etc.), metal oxides (e.g., iron oxide, aluminum oxide, zirconium oxide, magnesium oxide, manganese oxide, titanium oxide, niobium oxide, ruthenium oxide, etc.), metal hydroxides, metal peroxides, and so forth. For example, cationic polyelectrolytes may be electrodeposited with concurrent electrodeposition of metal phosphates, metal oxides, metal hydroxides and/or metal peroxides from metal salts. In this regard, various metal salts (e.g., metal chlorides, metal nitrates, etc.) are known to undergo cathodic deposition in the form of insoluble phosphates, oxides, hydroxides and/or peroxides. Additional inorganic materials that may be deposited include metal nitrides.

A few specific examples of cathodically electrodeposited cationic polyelectrolyte coatings and cathodically electrodeposited hybrid inorganic/cationic polyelectrolyte coatings are described in the following paragraphs, among many other possibilities. By further including a conductive polymer during electrodeposition (e.g., in covalent or non-covalent association with a cationic polyelectrolyte, as an independent species, etc.), coatings in accordance with the invention may be formed.

In certain embodiments, chitosan may be employed as a cationic polyelectrolyte for electrodeposition. Chitosan is a modified polysaccharide containing randomly distributed β-(1-4)-linked D-glucosamine and N-acetyl-D-glucosamine monomer units. Chitosan is produced commercially by the alkaline N-deacetylation of chitin, which is a cellulose-like polymer consisting primarily of unbranched chains of modified glucose, specifically N-acetyl-D-glucosamine. The degree of deacetylation in commercial chitosans generally ranges from 60 to 70 to 80 to 90 to 100% although essentially any degree of deacetylation is possible. Chitosan is positively charged in acidic to neutral solutions with a charge density that is dependent on the pH and the degree of deacetylation. The pka value of chitosan generally ranges from 6.1 to 7.0, depending on the degree of deacetylation. Thus, while substantially insoluble in distilled water, chitosan is generally soluble in dilute aqueous acidic solutions (e.g., pH~6.5 or less). Without wishing to be bound by theory, it is believed that, during electrodeposition in slightly acidic solutions, the electric field urges positively charged chitosan in the direction of the cathode. As the chitosan nears the cathode the pH increases due to the presence of electrogenerated base, causing the chitosan to lose its charge and form an insoluble deposit on the cathode surface. See, e.g., X. Pang et al., *Materials Chemistry and Physics* 94 (2005) 245-251.

With regard to the electrogenerated base, various cathodic reactions have been described which are capable of increasing solution pH (i.e., rendering it more basic) at the cathode. Commonly described examples of such reactions include, for example, $O_2 + 4H^+ + 4e^- \rightarrow 2\,H_2O$, where pH<7, $O_2 + 2\,H_2O + 4e^- \rightarrow 4\,OH^-$, where pH≧7, $2H^+ + 2\,e^- \rightarrow H_2$, where pH<7, and $2H_2O + 2e^- \rightarrow H_2 + 2OH^-$, where pH≧7, (The first two reactions require the presence of oxygen, whereas the latter two do not.) Regardless of the exact mechanism, processes are known to occur at the cathode in aqueous (i.e., water containing) solutions, which can result in an increase in pH at the cathode. The difference between the bulk solution pH and that of the solution adjacent to the cathode is said to increase with increasing current density. See, e.g., X. Pang et al., Langmuir, 20 (2004) 2921-2927 and the references cited therein.

As another example, J. Wang et al., J. Dent. Res. 83(4), 2004, 296-301, describe the formation of hybrid calcium phosphate/chitosan coatings through cathodic electrodeposition.

As another example, collagen has been reported to precipitate from solution by the local pH increase that occurs at the cathode. See, e.g., Y. Fan et al., Biomaterials 26 (2005) 1623-1632. It was theorized that, since the initial pH in the electrolyte (4.5-5.3) was below the isoelectric point of collagen (pH 5.5), the soluble free collagen molecules were positively charged and were driven towards the cathode as part of the electrodeposition mechanism. Id. These authors further report the simultaneous deposition of calcium phosphate minerals at the cathode, and they ascribe it to supersaturation based on the local pH increase at the cathode. Id.

In further examples, still other weak cationic polyelectrolytes may be deposited, for example, selected from PEI, PAH, poly-l-lysine, poly-l-arginine, etc. For instance, in discussing the electrodeposition of films of weak polyelectrolytes such as PEI and PAH, X. Pang et al., Langmuir 20 (2004) 2921-2927 note that relatively thick electrophoretic deposits can be obtained by this method.

PAH has been recently found to improve adhesion of endothelial cells without disturbing adhesion mechanism necessary to build a new endothelium. C. Boura et al, Biomaterials 26 (2005) 4568-4575.

In certain embodiments of the invention, an inorganic material is optionally co-deposited with a weak or strong cationic polyelectrolyte. For example, cationic polyelectrolytes may be electrodeposited with concurrent electrodeposition of metal oxides metal hydroxides, or metal peroxides from metal salts. Cathodic electrodeposition may be achieved, for example, via hydrolysis of metal ions or complexes by electrogenerated base to form oxide, hydroxide and peroxide deposits. See, e.g., I. Zhitomirsky, Journal of the European Ceramic Society 19 (1999) 2581-2587 and the references cited therein. Zhitomirsky specifically describes the cathodic formation of metal peroxides, in particular, titanium and niobium peroxides. Id.

For instance, electrodeposition of weak cationic polyelectrolytes (specifically PAH and PEI) and metallic oxides and/or hydroxides have been reported, including PAH-iron oxide, PAH-zirconia and PEI-zirconia coatings. See J. Cao et al., Materials Chemistry and Physics 96 (2006) 289-295 and X. Pang et al., Langmuir 20 (2004) 2921-2927. Without wishing to be bound by theory, it has been hypothesized that that the polyelectrolytes form polymer-metal ion complexes in metal salt solutions (e.g., PAH and PEI are known to form polymer-metal ion complexes) and that such polymer-metal ion complexes behave as positively charged polyelectrolytes, migrating to the cathode via electrophoresis. Id. In the higher pH environment at the cathode, free and complexed ions form insoluble metal hydroxides or oxides. Id. Moreover, the decrease in the charge of the polyelectrolyte with increasing pH reduces the electrostatic repulsion between the polyelectrolyte molecules and promotes their deposition. Id. See also N. Nagarajan et al., Electrochimica Acta 51 (2006) 3039-3045 who posit a similar mechanism in the formation of PEI-manganese oxide films.

Co-electrodeposition of strong cationic polyelectrolytes and metallic oxides and/or hydroxides have also been reported, including the formation of PDDA-zirconia films, PDDA-cerium films and PDDA-iron oxide films. See, e.g., I. Zhitomirsky et al. Materials Letters, 57 (2003) 1045-1050, I. Zhitomirsky et al., Canadian Metallurgical Quarterly, 41(4), 2002, 497-506, P. Bon et al., Materials Chemistry and Physics, 86(1), 2004, 44-50, and X. Pang et al., Surface & Coatings Technology, 195 (2005) 138-146, and the references cited therein. Without being bound by theory, it has been suggested that deposit formation is driven by the Coulombic attraction between the positively charged PDDA and negatively charged colloidal particles (e.g., particles comprising metal oxides and/or metal hydroxides, which as indicated above are believed to be formed at the cathode in the presence of electrogenerated base). The reported thickness of the composite films was in the range of 5-10 μm. Id.

Regardless of the precise deposition mechanism, techniques such as those described above, among others, can be used to cathodically deposit one or more types of cationic polyelectrolytes, which in turn may be co-deposited with one or more of the following: (a) one or more types of conductive polymer species (e.g., neutral and positively charged conductive polymer particles, complexes or block copolymers, such as those described above, etc.), (b) one or more types of optional inorganic materials (e.g., such as those discussed above), and (c) one or more types of optional therapeutic agents (e.g., neutral and positively charged therapeutic agents such as those described below). Co-deposition may be advantageous, for example, in that multiple deposition steps may be avoided.

"Therapeutic agents," "pharmaceuticals," "pharmaceutically active agents," "drugs" and other related terms may be used interchangeably herein and include genetic therapeutic agents, non-genetic therapeutic agents and cells. The optional therapeutic agents may be used singly or in combination. A wide variety of therapeutic agents can be employed in conjunction with the present invention, including those used for the treatment of a wide variety of diseases and conditions (i.e., the prevention of a disease or condition, the reduction or elimination of symptoms associated with a disease or condition, or the substantial or complete elimination of a disease or condition).

Where one or more types of therapeutic agents are present in the coatings of the invention, the coatings may comprise, for example, from 1 wt % or less to 2 wt % to 5 wt % to 10 wt % to 25 wt % or more of the therapeutic agents.

In some embodiments, the optional therapeutic agents are provided after deposition of a conductive-polymer-containing coating in accordance with the invention (e.g., one that includes one or more types of conductive polymers, one or more types of additional polymers and optionally one or more types of inorganic materials), for example, by contact with a solution that contains the therapeutic agent (e.g., by spraying, dipping, etc.)

In some embodiments, the optional therapeutic agents are electrodeposited, for example, by any of various mechanisms described above.

The optional therapeutic agents may be independently electrodeposited or co-deposited with one or more of the following: (a) one or more types of cationic polyelectrolytes, (b) one or more types of conductive polymers and (c) one or more types of inorganic materials. As indicated above, co-deposition may be advantageous, for example, in that multiple steps (e.g., those associated with post-loading of therapeutic agents into already-formed coatings) may be avoided.

In some embodiments, the optional therapeutic agent consists of or is covalently or non-covalently associated with a cationic polyelectrolyte. In the former case, coatings may be formed that comprise, for example, a pure therapeutic agent (where the therapeutic agent is a cationic polyelectrolyte) with embedded conductive polymer particles, among other possibilities.

Examples of therapeutic agents for use in connection with the present invention include: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, and (gg) VLA-4 antagonists and VCAM-1 antagonists.

Some preferred therapeutic agents include taxanes such as paclitaxel, sirolimus, everolimus, tacrolimus, zotarolimus, and other olimus family drugs, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic agents useful for the practice of the present invention are also disclosed in U.S. Pat. No. 5,733,925 to Kunz, the entire disclosure of which is incorporated by reference.

As previously indicated, in certain embodiments of the invention, the therapeutic agent is in the form of a soluble formulation, which can be, for example, entrapped during growth of conductive-polymer-containing coatings in accordance with the invention, or loaded after the formation of such coatings. For example, paclitaxel is commercially available as a soluble formulation in ethanol.

In certain embodiments of the invention, the therapeutic agent is a positively charged therapeutic agent.

For instance, a therapeutic agent may have an associated positive charge because it is inherently charged (e.g., because it has basic groups, which may be in salt form). A few examples of inherently charged cationic therapeutic agents include amiloride, digoxin, morphine, procainamide, and quinine, among many others.

A therapeutic agent may also have an associated positive charge because it is chemically modified to provide it with one or more charged entities.

For instance, therapeutic agents may be conjugated to cationic species including polycationic species (e.g., weak or strong cationic polyelectrolytes). Taking paclitaxel as a specific example, various charged forms of this drug, including various cationic forms of this drug are known, including paclitaxel N-methyl pyridinium mesylate. See, e.g., U.S. Pat. No. 6,730,699; Duncan et al., *Journal of Controlled Release* 74 (2001)135; Duncan, *Nature Reviews/Drug Discovery*, Vol. 2, May 2003, 347; Jaber G. Qasem et al, *AAPS Pharm Sci Tech* 2003, 4(2) Article 21. U.S. Pat. No. 6,730,699 describes paclitaxel conjugated to various polyelectrolytes including poly(l-lysine), poly(d-lysine), poly(dl-lysine), poly(2-hydroxyethyl-1-glutamine) and chitosan.

T.Y. Zakharian et al., *J. Am. Chem. Soc.*, 127 (2005) 12508-12509 describe a process for forming a fullerene-paclitaxel conjugate by covalently coupling paclitaxel-2'-succinate to a fullerene amino derivative. In the present invention, carboxylate-substituted therapeutic agents and their derivatives, including, for example, paclitaxel-2'-succinate, may be analogously coupled to other amine-containing compounds (e.g., cationic polyelectrolytes such as chitosan, PEI, PAH, PDDA, etc.) using a suitable linking chemistry, for instance, carbodiimide coupling. Similarly, amine-substituted therapeutic agents and their derivatives may be coupled to carboxyl-containing cationic polyelectrolytes, including, for example, N-succinyl-chitosan. Y. Kato et al, *Biomaterials* 25(5), 2004, 907-915.

Using the above and other strategies, a wide variety of therapeutic agents may be covalently linked or otherwise associated with a wide variety of cationic species, including cationic polyelectrolytes, thereby forming positively charged drugs and prodrugs.

A therapeutic agent may also have an associated charge because it is associated with a charged particle (e.g., attached to a charged particle or forming the core of a charged particle). For example, A. S. Zahr et al., *Biomacromolecules*, 8(6), 2007, 2004-2010 describe the encapsulation of solid core paclitaxel nanoparticles within a polymeric shell formed by electrostatic layer-by-layer self-assembly of alternating layers of PAH polycation and poly(styrene-4-sulfonate) (PSS) polyanion. In the present invention, the outer layer can be the PAH layer (rather than the PSS layer), giving the nanoparticles a positive charge.

Using methods and materials such as those described above, electrodeposited coatings may thus be provided that include (a) one or more types of cationic polyelectrolytes, (b) one or more types of conductive polymers, (c) optionally, one or more types of inorganic materials, and (d) optionally, one or more types of therapeutic agents, among other materials.

Coatings in accordance with the invention may be grown, for example, using a galvanostatic deposition regime with the current densities in the range for example from 1-10 mA/cm$^2$, among other possibilities. Rather than a galvanostatic regime, potentiostatic, pulsed or alternating current regimes can also be used, among others. The cathodic electrodeposition process may be performed, for example, at temperatures ranging from room temperature to about 80° C., among others. The electrodeposition process provides the ability to control coating stoichiometry and to tune other physico-chemical properties of the coatings, such as thickness and porosity, by adjusting current density, duration, reagent concentration and temperature, among other factors.

Figure 2A:
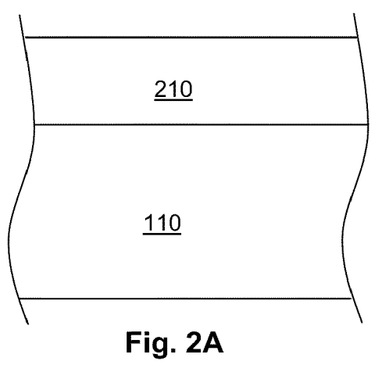
FIGS. 2A-2B are partial schematic cross-sectional views of medical devices in accordance with various embodiments of the invention.

In some embodiments, the conductive-polymer-containing coatings of the invention are in the form of a single layer. For example, referring now to FIG. 2A, a partial schematic cross-sectional view of a medical device in accordance with the invention is shown which includes a substrate 110 and a deposited layer 210 on the substrate which includes the following: a conductive polymer (e.g., particles of polypyrrole, polythiophene, polyaniline or PEDOT, among others, which may be associated with a positively charged species such as a polycation), an additional polymer (e.g., a cationic polyelectrolyte, such as chitosan, PEI, PAH, PDDA, polylysine or polyarginine, etc.), optionally, an inorganic material (e.g., oxides and/or hydroxides of iron, zirconium, magnesium, etc.) and, optionally, a therapeutic agent (e.g., an antirestenotic agent or an endothelial-cell-growth promoting agent, which may be provided with an associated polycation). Such embodiments may be advantageous in that hybrid materials may be produced during a single continuous growth process, for example, a single electrodeposition process.

As previously indicated, in some embodiments, conductive polymers are employed which are complexed, coated, covalently attached to or otherwise associated with a cationic polyelectrolyte material. Similarly, in some embodiments, therapeutic agents are employed which are complexed, coated, covalently attached to, or otherwise associated with a cationic polyelectrolyte material. In certain of these embodiments, the cationic polyelectrolyte material that is associated with the conductive polymer and/or the therapeutic agent may be the same as a co-deposited cationic polyelectrolyte (in other embodiments, on the other hand, a co-deposited cationic polyelectrolyte is not employed). For example, chitosan-associated conductive polymer and, optionally, chitosan-associated therapeutic agent may be co-deposited with chitosan using methods such as those previously described. Similarly, collagen-associated conductive polymer and, optionally, collagen-associated therapeutic agent may be co-deposited with collagen, or PAH-associated conductive polymer and, optionally, PAH-associated therapeutic agent may be co-deposited with PAH, and so forth.

In certain embodiments of the invention, PPy with associated PAH (e.g., PPy complexed, coated, covalently attached to or otherwise associated with PAH) is deposited. (The PPy with associated PAH may, or may not, be co-deposited with free PAH, with an optional therapeutic agent that is associated with PAH, with an optional inorganic material, and so forth.) As previously indicated PAH has been found to improve adhesion of endothelial cells, whereas polypyrrole is known to support human endothelial cells growth. Thus, such coatings are desirable for vascular implants (e.g., stents, etc.) wherein endothelial cell coverage is desired for optimum biocompatibility.

In certain embodiments, the coatings of the invention are formed from multiple electrodeposited layers.

Figure 2B:
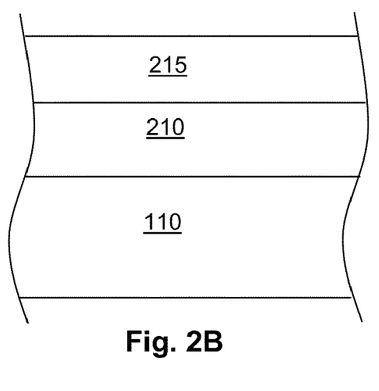

For example, referring now to FIG. 2B, a multilayer structure is shown on a substrate 110 (e.g., a metallic substrate) which includes the following: an electrodeposited conductive polymer layer 210 (e.g., polypyrrole, polythiophene, polyaniline or PEDOT, among others, associated with a positively charged species such as a polycation) and an outer layer 215 comprising a cationic polyelectrolyte (e.g., chitosan, PEI, PAH, PDDA, polylysine, polyarginine, etc.), an optional therapeutic agent (e.g., an antirestenotic agent or an endothelial-cell-growth promoting agent, which may be associated with a polycation), and an optional inorganic material (e.g., oxides and/or hydroxides of iron, zirconium, etc.).

Referring again to FIG. 2B, in one alternative embodiment, a multilayer structure is shown on a substrate 110 (e.g., a metallic substrate) which includes the following: an electrodeposited drug layer 210 (e.g., an antirestenotic agent or an endothelial-cell-growth promoting agent with an associated polycation such as chitosan, PAH, PEI, PDDA, polylysine or polyarginine, among others) and an outer layer 215 comprising a conductive polymer (e.g., polypyrrole, polythiophene, polyaniline or PEDOT, among others, which may be associated with a positively charged species such as a polycation), optionally, a cationic polyelectrolyte (e.g., chitosan, PEI, PAH, PDDA, polylysine, polyarginine, etc.) that is not associated with a conductive polymer and, optionally, an inorganic material (e.g., oxides and/or hydroxides of iron, zirconium, etc.).

An additional desirable feature of the present invention is that it allows metallic substrates to be readily anodized (e.g., to achieve surface roughening which can improve adhesion) with essentially no further cost. This may be done, for example, by application of an appropriate anodic electrical potential while immersing the metallic substrate in a suitable electrolyte, typically an aqueous electrolytic solution. Examples of aqueous electrolytic solutions include acidic solutions (e.g., solutions of one or more of hydrochloric acid, sulfuric acid, phosphoric acid, and nitric acid, among others), basic solutions (e.g., KOH, NaOH, $CaOH_2$, etc.), and neutral solutions (e.g., sodium nitrate, sodium chloride, potassium chloride, potassium sulfate, etc.)

Figure 3A:
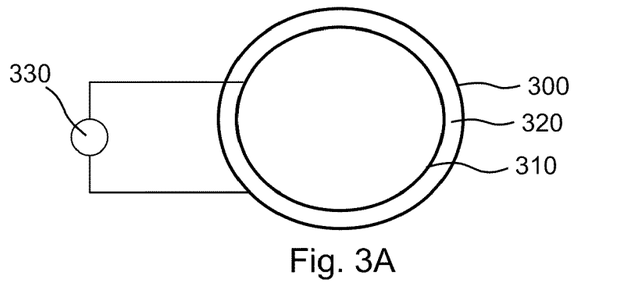
FIGS. 3A-3C and 4 are schematic illustrations of electrochemical apparatuses for anodizing a stent and/or for forming an electrodeposited coating on a tubular medical device such as a stent, in accordance with various embodiments of the present invention.

FIG. 3A is a schematic illustration of an electrochemical apparatus for anodizing a tubular substrate surface (e.g., a stent surface) and/or forming an electrodeposited coating on a tubular substrate surface in accordance with an embodiment of the present invention and includes a stent 300 (end view), a cylindrical counter-electrode 310 (end view) and a suitable liquid medium 320, which is placed between the stent 300 and the counter-electrode 310. Anodization of the stent 300 or formation of an electrodeposited coating on the stent 300 is conducted via potentiostat 330. Using such an apparatus, at least the luminal surface of the stent may be anodized and/or provided with an electrodeposited coating, in accordance with the present invention.

Figure 3B:
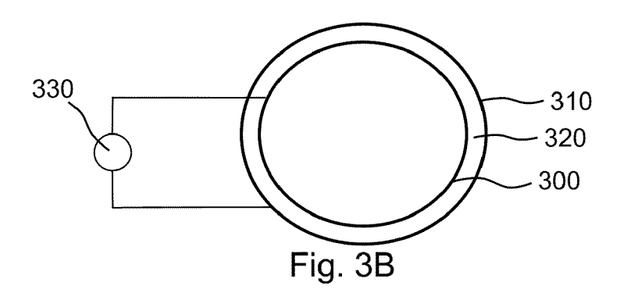

FIG. 3B is a schematic illustration of another electrochemical apparatus for anodizing a tubular substrate surface (e.g., a stent surface) and/or forming an electrodeposited coating on a tubular substrate surface, in accordance with an embodiment of the present invention. As in FIG. 3A, a suitable liquid medium 320 and placed between the stent 300 (end view) and the counter-electrode 310 (end view) of FIG. 3B. Moreover, anodization of the stent 300 or formation of an electrodeposited coating on the stent 300 is conducted via potentiostat 330 in FIG. 3B. However, FIG. 3B is unlike FIG. 3A in that the positions of the stent 300 and the cylindrical counter-electrode 310 are reversed. Using such an apparatus, at least the abluminal surface of the stent may be anodized and/or provided with an electrodeposited coating, in accordance with the present invention.

Figure 3C:
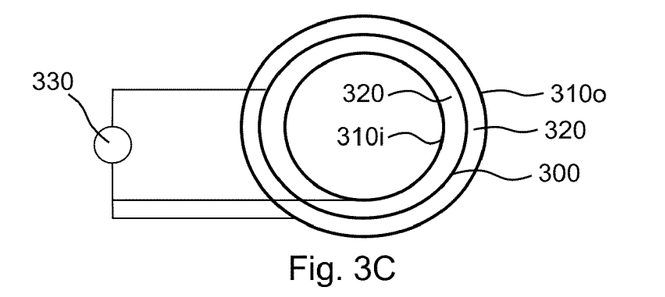

FIG. 3C is a schematic illustration of another electrochemical apparatus for anodizing a tubular substrate surface (e.g., a stent surface) and/or forming an electrodeposited coating on a tubular substrate surface, in accordance with an embodiment of the present invention. The apparatus shown includes a stent 300 (end view), a compound counter-electrode comprising two cylindrical elements, outer element 310o (end view) and inner element 310i (end view), and a suitable liquid medium 320, which is placed between the stent 300 and cylindrical elements 310. Anodization of the stent 300 or formation of an electrodeposited coating on the stent 300 is conducted via potentiostat 330. Using such an apparatus, the luminal and abluminal surfaces of the stent may be anodized and/or provided with an electrodeposited coating, in accordance with the present invention.

Figure 4:
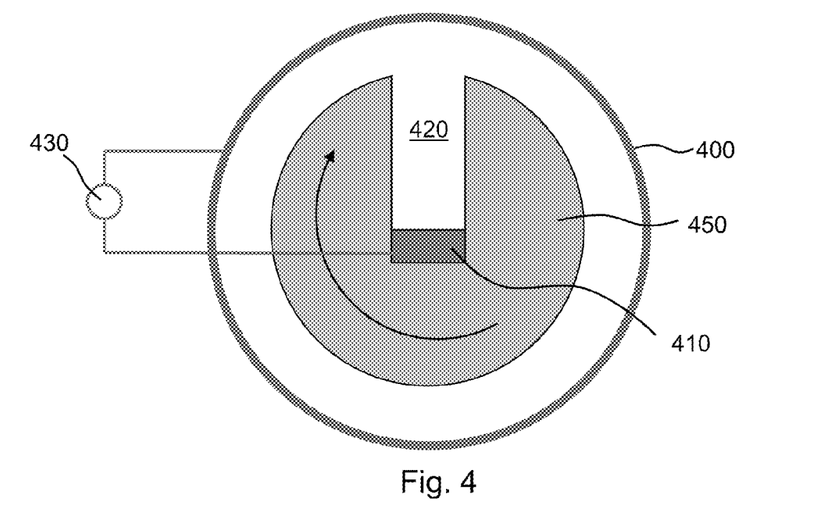

Coating thickness depends upon current distribution and thus the preceding apparatuses may require precise positioning between the various electrodes. Another approach is to use a system like described in FIG. 4, which, like FIG. 3A, is a schematic illustration of an electrochemical apparatus for anodizing a tubular substrate surface (e.g., a stent surface) and/or forming an electrodeposited coating on a tubular substrate surface in accordance with an embodiment of the present invention. It includes a stent 400 (end view), a counter-electrode 410 (end view) and a suitable liquid medium 420, which is placed between the stent 400 and the counter-electrode 410. Unlike FIG. 3A, however, the apparatus of FIG. 4 is provided with an electrical isolator 450, which along with the counter-electrode 410 is rotated in the center of the stent (e.g., the electrical isolator 450 may be formed from a slotted, non-conductive rod made, for instance, from polyoxymethylene (POM), tradename DERLIN, and the counter-electrode 410 may be located in the bottom of the slot). As above, anodization of the stent 400 or formation of an electrodeposited coating on the stent 400 is conducted via potentiostat 430. Using such an apparatus, at least the luminal surface of the stent may be anodized and/or provided with an electrodeposited coating, in accordance with the present invention. For the device of FIG. 4, any mismatch between the stent 400 and the counter-electrode 410 is now much less of a concern. In this regard, it will be clear that the deposition is primarily taking place via the slot of the rod 450, and the deposition process may be followed by measuring the current. Consequently, a cyclic decrease or increase in deposition while rotating the rod in the stent (e.g., due to an axial offset/mismatch) may be counteracted by varying the rotational speed or/and the voltage during the course of rotation. Another advantage of using such a slotted rod is that one could establish a non-uniform deposition of the coating, if desired. This could be useful, for example, in devices that don't require a uniform drug distribution, for instance, a bifurcation device such as a Boston Scientific Petal™ type stent in which it may be desirable to deposit more drug in the area of the Petal.

EXAMPLE 1

Vascular stents made of magnesium metal are electropolished using an applied anodic potential in a solution of phosphoric acid and ethanol, followed by drying in hot air. PEDOT nanoparticles are formed as described by J. W. Choi et al., Synthetic Metals, 141(3), 2004, 293-299 and coated with chitosan, for example, by electrostatic assembly (if desired, the nanoparticles may be exposed to a negatively charged polyelectrolyte such as such as polystyrene sulfonate or another suitable polyanion, prior to exposure to chitosan). The stents are subjected to a cathodic deposition step in which the chitosan-coated nanoparticles are deposited on the stent surface from a slightly acidic bulk solution, both in the presence and absence of free chitosan as a soluble polyelectrolyte in the bulk solution. Deposition is also conducted in the presence and absence of calcium phosphate. See J. Wang et al., J. Dent. Res. 83(4), 2004, 296-301. Other phosphates, such as magnesium phosphate, iron phosphate or zinc phosphate, may be substituted for calcium phosphate.

EXAMPLE 2

Vascular stents electropolished as described in Example 1 are subjected to a cathodic deposition step in which a block copolymer having one or more polycation blocks and one or more conductive polymer blocks (i.e., a chitosan-polypyrrole diblock copolymer) is deposited on the stent surface from a slightly acidic bulk solution, both in the presence and absence of free chitosan as a soluble polyelectrolyte in the bulk solution.

EXAMPLE 3

Vascular stents electropolished as described in Example 1 are subjected to a cathodic deposition step in which a block copolymer having one or more polycation blocks and one or more conductive polymer blocks (i.e., a chitosan-PEDOT diblock copolymer) is deposited on the stent surface from a slightly acidic bulk solution, both in the presence and absence of free chitosan as a soluble polyelectrolyte in the bulk solution.

EXAMPLE 4

Water soluble a complexes (i.e., PEDOT-PAH complex, PEDOT-PEI complex, PEDOT-PDDA complex, PPy-PAH complex, PPy-PEI complex, PPy-PDDA complex) are formed in a procedure analogous to that described in F. F. Bruno et al., Mat. Res. Soc. Symp. Proc. Vol. 736, 2003, D7.13.1-D7.13.6 from 3,4-dimethoxythiophene or pyrrole monomers using poly(ethylene glycol) modified hematin (PEG-Hematin) as a catalyst and PAH, PEI or PDDA as cationic polyelectrolytes (which provide water solubility). Vascular stents electropolished as described in Example 1 are subjected to a cathodic deposition step in which the preceding complexes are deposited on the stent surface, both in the presence and absence of soluble polyelectrolyte (PAH, PEI, PDDA) in the bulk solution. Deposition is also conducted in the presence and absence of one or more of zirconium oxide, manganese oxide, iron oxide, titanium niobium peroxide, and niobium peroxide as described above.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device that comprises a conductive substrate and a cathodically electrodeposited coating over the substrate, said electrodeposited coating comprising a conductive polymer and a cationic polyelectrolyte, wherein (a) the conductive polymer is covalently linked to the cationic polyelectrolyte or (b) the electrodeposited coating comprises nanoparticles that comprise said conductive polymer, and wherein the conductive polymer is selected from the group consisting of polyaniline, poly(phenylene vinylene), polypyrrole, polythiophene, and derivatives and copolymers of the same.

2. The implantable or insertable medical device of claim 1, wherein said conductive substrate is a metallic substrate.

3. The implantable or insertable medical device of claim 1, wherein said conductive substrate is a biodegradable metallic substrate.

4. The implantable or insertable medical device of claim 3, wherein the biodegradable metallic substrate is a material selected from the group consisting of magnesium, magnesium alloys, iron, iron alloys, zinc, and zinc alloys.

5. The implantable or insertable medical device of claim 1, wherein the electrodeposited coating comprises nanoparticles that comprise said conductive polymer.

6. The implantable or insertable medical device of claim 5, wherein said cationic polyelectrolyte is covalently or non-covalently attached to a surface of the nanoparticles.

7. The implantable or insertable medical device of claim 1, wherein the conductive polymer is covalently linked to the cationic polyelectrolyte.

8. The implantable or insertable medical device of claim 1, wherein said cationic polyelectrolyte is a biodegradable cationic polyelectrolyte.

9. The implantable or insertable medical device of claim 1, wherein the cationic polyelectrolyte is selected from chitosan, collagen, poly(allyamine hydrochloride) (PAH), polyethyleneimine (PEI), poly(diallyldimethylammonium chloride) (PDDA), polylysine, polyarginine, or a combination thereof.

10. The implantable or insertable medical device of claim 1, further comprising a calcium phosphate species, a metal oxide, a metal hydroxide or a combination thereof.

11. The implantable or insertable medical device of claim 10, wherein the cationic polyelectrolyte is selected from chitosan, collagen, PAH, PEI and PDDA.

12. The implantable or insertable medical device of claim 1, further comprising a therapeutic agent.

13. The implantable or insertable medical device of claim 12, wherein the therapeutic agent is an antirestenotic agent or an endothelial-cell-growth-promoting agent.

14. The implantable or insertable medical device of claim 12, wherein the electrodeposited coating comprises particles that comprise said therapeutic agent.

15. The implantable or insertable medical device of claim 14, wherein said cationic polyelectrolyte that is covalently or non-covalently attached to a surface of the particle.

16. The implantable or insertable medical device of claim 12, wherein the therapeutic agent is covalently bound to the cationic polyelectrolyte.

17. The implantable or insertable medical device of claim 1, wherein the electrodeposited coating is a single layer coating.

18. The implantable or insertable medical device of claim 1, wherein the electrodeposited coating is a multilayer coating.

19. The implantable or insertable medical device of claim 18, where said multilayer coating comprises a first cathodically electrodeposited layer comprising said conductive polymer and a second coating cathodically electrodeposited layer, disposed over the first cathodically electrodeposited layer, which comprises said cationic polyelectrolyte.

20. The implantable or insertable medical device of claim 18, where said multilayer coating comprises a first cathodically electrodeposited layer comprising a therapeutic agent, and a second coating cathodically electrodeposited layer, disposed over the first cathodically electrodeposited layer, which comprises said conductive polymer and said cationic polyelectrolyte.

21. The implantable or insertable medical device of claim 1, wherein said medical device is a stent.

22. An implantable or insertable medical device that comprises a conductive substrate and a cathodically electrodeposited coating over the substrate, said electrodeposited coating comprising a conductive polymer and a cationic polyelectrolyte, wherein (a) the conductive polymer is covalently linked to the cationic polyelectrolyte or (b) the electrodeposited coating comprises nanoparticles that comprise said conductive polymer, and wherein the conductive polymer is selected from the group consisting of poly(3-alkyl pyrrole), polythiophene, poly(3-alkyl thiophene), polyaniline, poly(aniline-co-2-anisidine), poly(phenylene vinylene) and poly(bis-(dialkylamino)phenylene vinylene).

23. An implantable or insertable medical device that comprises a conductive substrate and a cathodically electrodeposited coating over the substrate, said electrodeposited coating comprising a conductive polymer and a cationic polyelectrolyte, wherein (a) the conductive polymer is covalently linked to the cationic polyelectrolyte or (b) the electrodeposited coating comprises nanoparticles that comprise said conductive polymer, and wherein the conductive polymer is selected from the group consisting of polypyrrole and poly(3,4-ethylenedioxythiophene) (PEDOT).

24. An implantable or insertable medical device that comprises a conductive substrate and a cathodically electrodeposited coating over the substrate, said electrodeposited coating comprising a conductive polymer and a cationic polyelectrolyte, wherein the electrodeposited coating comprises nanoparticles that comprise said conductive polymer, and wherein said nanoparticles are selected from polypyrrole nanoparticles, polythiophene nanoparticles, polyaniline nanoparticles, poly(3,4-ethylenedioxythiophene) (PEDOT) nanoparticles, and combinations thereof.

* * * * *